(12) United States Patent
Badejo et al.

(10) Patent No.: US 6,607,631 B1
(45) Date of Patent: Aug. 19, 2003

(54) ADHESIVE COMPOSITIONS WITH REDUCED COEFFICIENT OF FRICTION

(75) Inventors: Ibraheem T. Badejo, Morrisville; Wendy Y. Su, Durham; Keith R. D'Alessio, Cary; Jerry Jonn, Raleigh; Julian A. Quintero, Raleigh; Michelle Knotts, Raleigh; Timothy P. Hickey, Raleigh; Lawrence H. Mainwaring, Raleigh; Upvan Narang, Raleigh, all of NC (US)

(73) Assignee: Closure Medical Corporation, Raleigh, NC (US)

( * ) Notice: Subject to any disclaimer, the term of this patent is extended or adjusted under 35 U.S.C. 154(b) by 0 days.

(21) Appl. No.: 09/657,912

(22) Filed: Sep. 8, 2000

(51) Int. Cl.⁷ .................. C09J 183/04; A61K 31/74; C08K 9/06
(52) U.S. Cl. ............... 156/327; 424/78.03; 424/78.06; 424/78.02; 156/325; 156/326; 156/329; 523/212
(58) Field of Search .................. 156/327, 325, 156/326, 329; 424/78.03, 78.06, 78.02; 523/212

(56) References Cited

U.S. PATENT DOCUMENTS

| | | | |
|---|---|---|---|
| 2,721,858 A | 10/1955 | Joyner et al. | |
| 3,223,083 A | 12/1965 | Cobey | |
| 3,254,111 A | 5/1966 | Hawkins et al. | |
| 3,554,990 A | 1/1971 | Quinn et al. | |
| 3,636,361 A | 1/1972 | Bowers | |
| 3,722,599 A | 3/1973 | Robertson et al. | |
| 3,940,362 A | 2/1976 | Overhults | |
| 3,995,641 A | 12/1976 | Kronenthal et al. | |
| 4,012,402 A | 3/1977 | Buck | |
| 4,105,715 A | 8/1978 | Gleave | |
| 4,180,911 A | 1/1980 | Bullock | |
| 4,313,865 A | 2/1982 | Teramoto et al. | |
| 4,364,876 A | 12/1982 | Kimura et al. | |
| 4,393,183 A | 7/1983 | Kimura et al. | |
| 4,477,607 A | 10/1984 | Litke | |
| 4,533,422 A | 8/1985 | Litke | |
| 4,560,723 A | 12/1985 | Millet et al. | |
| 4,636,539 A | 1/1987 | Harris et al. | |
| 4,650,826 A | 3/1987 | Waniczek et al. | |
| 4,686,247 A | 8/1987 | Yosida | |
| 4,705,836 A | 11/1987 | Ohtsuka et al. | |
| 4,713,405 A | 12/1987 | Koga et al. | |
| 4,720,513 A | 1/1988 | Kameyama et al. | |
| 4,764,545 A | 8/1988 | Yosida | |
| RE32,889 E | 3/1989 | Litke | |
| 4,837,260 A | 6/1989 | Sato et al. | |
| 4,906,317 A | 3/1990 | Liu | |
| 4,912,153 A | 3/1990 | Jermias et al. | |
| 5,034,456 A | 7/1991 | Katsumura et al. | |
| 5,039,753 A | 8/1991 | Woods et al. | |
| 5,140,084 A | 8/1992 | Mikuni et al. | |
| 5,214,093 A | 5/1993 | Nell et al. | |
| 5,248,708 A | 9/1993 | Uemura et al. | |
| 5,328,687 A | 7/1994 | Leung et al. | |
| 5,356,986 A | 10/1994 | Stewart et al. | |
| 5,373,035 A | 12/1994 | Uemura et al. | |
| 5,386,047 A | 1/1995 | Nakos et al. | |
| 5,466,764 A | 11/1995 | Hiraoka | |
| 5,514,371 A | 5/1996 | Leung et al. | |
| 5,514,372 A | 5/1996 | Leung et al. | |
| 5,575,997 A | 11/1996 | Leung et al. | |
| 5,582,834 A | 12/1996 | Leung et al. | |
| 5,624,669 A | 4/1997 | Leung et al. | |
| 5,902,443 A | 5/1999 | Kanakubo et al. | |
| 5,928,611 A | 7/1999 | Leung | |
| 6,143,352 A | 11/2000 | Clark et al. | |
| 6,143,805 A | 11/2000 | Hickey et al. | |
| 6,183,593 B1 * | 2/2001 | Narang et al. | .......... 156/327 |
| 2001/0004655 A1 * | 6/2001 | Takahashi et al. | .......... 524/65 |

FOREIGN PATENT DOCUMENTS

| | | |
|---|---|---|
| DE | 431 7886 | 12/1993 |
| EP | 0 611 565 A | 8/1994 |
| EP | 0 774 482 A | 5/1997 |
| FR | 1389441 | 6/1965 |
| JP | 57-70169 | 4/1982 |
| JP | 57-70171 | 4/1982 |
| JP | 63-60961 | 3/1988 |
| JP | 3-126782 | 5/1991 |
| JP | 3-296581 | 12/1991 |
| JP | 4-8780 | 1/1992 |
| JP | 4-9388 | 1/1992 |
| JP | 4-146982 | 5/1992 |
| JP | 6-100838 | 4/1994 |
| JP | 6-122853 | 5/1994 |
| JP | 6-240209 | 8/1994 |
| JP | 11-302602 | 11/1999 |
| SU | 668332 * | 11/1983 |
| SU | 448750 * | 3/1992 |
| WO | WO 99/42142 | 8/1999 |
| WO | WO 01/46327 A2 | 6/2001 |

* cited by examiner

Primary Examiner—Thurman K. Page
Assistant Examiner—Blessing Fubara
(74) Attorney, Agent, or Firm—Oliff & Berridge, PLC

(57) ABSTRACT

A polymerizable monomer adhesive composition includes a 1,1-disubstituted ethylene monomer and at least one slip additive, where the slip additive causes a polymer film formed from the monomer to have a lower coefficient of friction than in an absence of the slip additive. The slip additive can be selected from, inter alia, fluorinated monomers or polymers, fluorinated additives, siloxane-containing monomers or polymers, siloxane-containing additives, fluorinated siloxanes, and long chain fatty acid esters. The slip additive can also form a second phase in a resultant polymer film, where the second phase is soluble in the monomer but is insoluble or substantially insoluble in the polymer.

99 Claims, No Drawings

ADHESIVE COMPOSITIONS WITH REDUCED COEFFICIENT OF FRICTION

BACKGROUND OF THE INVENTION

1. Field of Invention

The present invention relates to adhesive compositions, more particularly to polymerizable monomeric adhesive compositions providing reduced coefficients of friction in the polymerized adhesive product. The present invention is also related to methods of making and using such adhesive compositions.

2. Description of Related Art

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made the α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present in the air or on moist surfaces such as animal (including human) tissue. Monomers of α-cyanoacrylates are anionically polymerizable or free radical polymerizable, or polymerizable by zwitterions or ion pairs to form polymers. Once polymerization has been initiated, the cure rate can be very rapid.

Medical applications of 1,1-disubstituted ethylene adhesive compositions include use as an alternate or an adjunct to surgical sutures and/or staples in wound closure, as well as for covering and protecting surface wounds such as lacerations, abrasions, burns, stomatitis, sores, minor cuts and scrapes, and other wounds. When an adhesive is applied to surfaces to be joined, it is usually applied in its monomeric form, and the resultant polymerization gives rise to the desired adhesive bond.

U.S. Pat. No. 5,928,611 to Leung discloses an applicator tip, and adhesive compositions useful therewith, having a polymerization or cross-linking initiator or accelerator disposed on or in a solid support in the applicator tip. The adhesive composition includes polymerizable monomers such as 1,1-disubstituted ethylene monomers and additives, such as polymerization inhibitors or stabilizers, viscosity modifiers, free radical scavengers, pH modifiers, other monomers, formaldehyde scavengers, colorants, lubricants, release or transfer agents, surfactants, defoamants, and plasticizers.

U.S. Pat. No. 5,928,611 to Clark et al. likewise discloses biocompatible cyanoacrylate adhesive compositions that include a polymerizable cyanoacrylate monomer, plasticizing agent, an acidic stabilizing agent and an initiator. The adhesive composition can also include various additives.

Other adhesive compositions are disclosed in, for example, U.S. Pat. Nos. 5,514,371, 5,514,372, 5,575,997, 5,624,669, and 5,582,834 to Leung et al. The adhesive composition can include various additives.

Although the various adhesive compositions have exhibited remarkable success and have found wide-spread use, several disadvantages have been noted with the materials. In particular, a film formed of the adhesive compositions, such as would be applied over a surface to bond adjoining pieces or over a wound or abrasion, sometimes has drawbacks in terms of the coefficient of friction of the film, and the tendency of the film to attract and retain dirt and lint. Both of these drawbacks are particularly evident in the medical field.

For example, when adhesive compositions are used to form polymer films in the medical field, reduced friction and reduced dirt attraction are particularly desired. Reduced friction is desired, for example, to reduce frictional rubbing of the adhesive film by adjoining surfaces such as clothing, bed sheets, prostheses, casts, bandages, and the like. Likewise, reduced dirt attraction is desired to improve the appearance, and perceived cleanliness, of the applied adhesive film.

Furthermore, it is desired in areas of the medical field to provide an adhesive composition that is easier to remove from the application site. While high degrees of adhesion are important in many uses, some uses require that the adhesion be balanced against a need to remove the adhesive without damaging the underlying tissue or skin or other substrate. For example, polymer adhesive films formed from many adhesive compositions are difficult or painful to remove, even from healthy and unbroken skin. However, where the skin or tissue surfaces are injured, removal of the polymeric film therefrom can be painful, and may cause further skin or tissue injury. A polymer adhesive film that is more easily removed, while still retaining its adhesion properties, would be very helpful and desired.

SUMMARY OF THE INVENTION

The present invention overcomes the above-described drawbacks by providing adhesive compositions that include friction reducing or slip enhancing agents. The friction reducing agents provide one or more advantageous benefits to the formed polymeric film. In particular, the friction reducing agents provide one or more of reduced coefficient of friction in the resultant formed polymer film, increased ease of removal of the film, and reduced dirt and lint attraction and retention on the surface of the polymer film. The present invention thereby provides adhesive compositions with increased utility, particularly in the medical field.

In particular, embodiments of the present invention provides a polymerizable monomer adhesive composition, comprising:

a 1,1-disubstituted ethylene monomer; and at least one slip additive, wherein said slip additive causes a polymer film formed from said monomer to have a lower coefficient of friction than in an absence of said slip additive.

In embodiments, the present invention provides a two-phase polymerizable monomeric adhesive composition, comprising:

a first phase comprising a 1,1-disubstituted ethylene monomer; and a second phase comprising a friction reducing agent, wherein said second phase is soluble in said first phase but said second phase is insoluble or substantially insoluble in a polymer formed from said first phase.

In embodiments, the present invention provides a two-phase polymeric adhesive composition, comprising:

a first phase comprising a polymer formed from a 1,1-disubstituted ethylene monomer; and a second phase comprising a friction reducing agent, wherein said second phase is soluble in said 1,1-disubstituted ethylene monomer but is insoluble or substantially insoluble in said polymer.

DETAILED DESCRIPTION OF PREFERRED EMBODIMENTS

Above and other objects of the present invention are achieved by including in the adhesive composition at least one slip additive or friction reducing agent. The slip additive or friction reducing agent is preferably solubilized in both the monomer composition as well as the resulting polymer composition, although solubility in both compositions is not required. In fact, benefits are also provided where the slip additive or friction reducing agent is solubilized in the monomer, but is not soluble (i.e., insoluble) or substantially insoluble in the resulting polymer.

Accordingly, in embodiments of the present invention, the friction reducing agent can be, for example, homogeneously dispersed in the resulting polymer film, or it can form a second phase that is insoluble or substantially insoluble in the polymer. When homogeneously dispersed in the polymer, the friction reducing agent can be, for example, chemically bonded into the polymer network, or it can be homogeneously dispersed without chemical bonding into the polymer network. Likewise, where the friction reducing agent is not soluble or substantially insoluble in the resulting polymer, it can be initially either homogeneously dispersed or not in the polymer network, although it may elute from the polymer network and/or form a distinct second phase either immediately or over time. By "substantially insoluble" it is meant that the slip additive or friction reducing agent is soluble in the polymer in an amount of no more than 0 percent by weight.

According to the present invention, a "friction reducing agent," also referred to as a "slip additive," is a component of the adhesive composition that provides the resultant formed polymer film with a decreased coefficient of friction as compared to a comparable polymer film not including the friction reducing agent. Thus, the friction reducing agent causes the resultant polymer film to have a more slippery or silky or slick feel, with reduced friction between the polymer film and materials that come into contact with the polymer film. The friction reducing effect is apparent at least in terms of the dynamic coefficient of friction, and can also be apparent in the static coefficient of friction. In embodiments, the slip additive or friction reducing agent can also have the effect of apparent friction reduction, without reducing per se the coefficient of friction. That is, the slip additive or friction reducing agent can have the effect of providing an apparent more slick or slippery surface, while having either no effect or an increasing effect on the actual coefficient of friction. This effect may be particularly apparent in embodiments where the slip additive or friction reducing agent forms a second phase in the polymer film.

According to the present invention, the dynamic coefficient of friction is reduced by at least 10%, as compared to a comparable polymer film formed from a corresponding adhesive composition not including the friction reducing agent. In embodiments, the dynamic coefficient of friction is reduced by at least 20% or 30%, or more preferably by at least 40% or 50%, as compared to a comparable polymer film formed from an adhesive composition not including the friction reducing agent. In other embodiments, the dynamic coefficient of friction is reduced by at least 60% or 70%, or more preferably by at least 80% or 90%, as compared to a comparable polymer film formed from an adhesive composition not including the friction reducing agent. Similar reductions can also be realized in the static coefficient of friction.

In embodiments, the coefficient of friction, in particular the dynamic coefficient of friction, is reduced to a level 0.8 or less, such as about 0.60 or less, or about 0.55 or less. Preferably, the coefficient of friction is reduced to a level of about 0.50 or less, or about 0.45 or less. More preferably, the coefficient of friction is reduced to a level of about 0.40 or less, or 0.35 or less. Preferably, the coefficient of friction is measured based on the a composition containing only the polymerizable monomer and the slip additive or friction reducing agent, i.e., not including other additives. However, the coefficient of friction can also be measured based on a complete adhesive formulation, including the polymerizable monomer and the slip additive or friction reducing agent, as well as one or more additional additives. The above mentioned preferred friction reductions and levels of coefficient of friction apply equally to either measurement approach. In embodiments, the coefficient of friction can also be measured according to ASTM D1894-95, the entire disclosure of which is incorporated herein by reference.

According to the present invention, suitable friction reducing agents include, but are not limited to, fluorinated monomers and polymers, fluorinated additives, siloxane-containing monomers and polymers, siloxane-containing additives, long chain fatty acid esters, mixtures thereof, and the like.

The friction reducing agent can be incorporated into the adhesive composition in any suitable and/or desirable amount. Inclusion of the friction reducing agent should provide the desired effect of reducing the coefficient of friction, while not rendering the adhesive composition unsuitable for its intended use, such as by prematurely polymerizing the composition or destroying the adhesion characteristics of the composition. Generally, the friction reducing agent can be incorporated into the adhesive composition in an amount of from about 0.05 or less to about 25% or more by weight, based on a total weight of the composition. Preferably, the friction reducing agent is incorporated into the adhesive composition in an amount equal to or greater than 0.1 or 0.5 or 1.0% by weight, based on a total weight of the composition, and in an amount of less than or equal to 15 or 10 or 5% by weight, based on a total weight of the composition. Preferably, the friction reducing agent is incorporated into the adhesive composition in an amount of from about 0.5 to about 3% by weight, based on a total weight of the composition. Amounts outside of these ranges can also be used.

Examples of suitable fluorinated monomers and polymers include, but are not limited to, fluorinated 1,1-disubstituted ethylene monomers. Particularly preferred suitable fluorinated monomers and polymers include, but are not limited to, fluorinated α-cyanoacrylates such as alkyl α-cyanoacrylates having an alkyl chain length of from about 1 to about 20 carbon atoms, preferably from about 2 to about 12 carbon atoms. Examples of such fluorinated alkyl α-cyanoacrylates include, for example, fluorinated ethyl, butyl, and octyl α-cyanoacrylates. Other particularly preferred suitable fluorinated monomers and polymers include, for example, fluorinated cyanopentadienoates.

When using fluorinated monomers and polymers, it is preferred that the fluorination be present in as high a degree as possible, and preferably at least in portions of the monomer and polymer located away from the polymer backbone.

Thus, for example, examples of suitable fluorinated α-cyanoacrylates include, but are not limited to, monomers of formula (I):

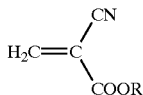
(I)

wherein R is a fluorinated alkyl group having from 1 to about 20 carbon atoms, preferably from about 2 to about 12 carbon atoms. Thus, for example, R can be represented as $C_nH_{2n+1-x}F_x$, where n is an integer from 1 to 20, preferably 2 to 12, and x is an integer from 1 to n. Preferably, x is an integer from 1 to n−1 when n is 2 or more. Thus, for example, suitable fluorinated alkyl α-cyanoacrylates include octafluorobutyl cyanoacrylate (formula Ia) and hexadecafluorooctyl cyanoacrylate (formula Ib):

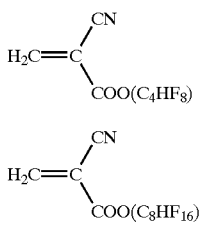
(Ia)

(Ib)

In embodiments, R in Formula I is preferably at least 20% fluorinated (i.e., that at least 20 percent by number of the hydrogen atoms in the group are replaced fluorine atoms), more preferably at least 50% fluorinated, and even more preferably at least 75% fluorinated.

Polymers of the above monomeric units may also be included in the adhesive composition, in embodiments. Thus, for example, poly(fluorinated cyanoacrylate) can be used as a friction reducing agent. Thus, for example, a poly(octafluorobutyl cyanoacrylate of the formula II can be used:

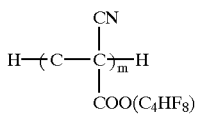
(II)

where m represents the number of repeating units in the polymer. Where the fluorinated polymer is added to the adhesive composition as a separate component, the polymer is preferably a low molecular weight polymer in which m ranges, for example, from about 2 to about 2000 or more, preferably from about 2 to about 1000 or from about 500 to about 1800, more preferably from about 100 to about 500 or from about 1000 to about 1700.

Although the above description has referred to the monomers and polymers as being fluorinated, the monomers and polymers are not limited thereto. Rather, any suitable halogenated monomers and polymers can be used. Suitable halogens thus include fluorine, chlorine, bromine, and iodine, with fluorine being preferred, so long as they provide the desired frictional properties.

Preferably, in embodiments of the present invention where fluorinated monomers and polymers are used as the friction reducing agent, it is preferred, although not required, that the fluorinated monomer or polymer not be the compound 5,8-bistrifluoromethyl-5,7,7,8,10,10,11,11,12,12,12-undecafluoro-3,6,9-trio xadodecyl alpha-cyanoacrylate.

In embodiments of the present invention it is also preferred, although not required, that the fluorinated monomers not be of the following formula:

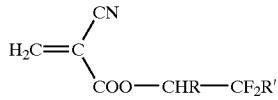

wherein R is hydrogen, methyl or ethyl and R' is —F, —CF$_3$, or —(CF$_2$)$_n$H where n is an integer of 1 to 3.

However, in embodiments of the present invention where the above less preferred monomers are used as friction reducing agents, it is preferred that the monomers be used in amounts of less than 50 weight percent, based on the total composition. Preferably, the fluorinated monomer is used in amount of less than 40 weight percent or less than 30 weight percent, based on the total composition. More preferably, the fluorinated monomer is used in amount of less than 20 weight percent or less than 10 weight percent, based on the total composition.

In embodiments, it is preferred that when fluorinated monomers are used as the friction reducing agent, they be used in a minor amount in conjunction with a major amount of non-fluorinated polymerizable adhesive monomer. In embodiments where fluorinated monomers are used as the friction reducing agent in combination with the non-fluorinated polymerizable adhesive monomer to form the adhesive composition, it is preferred that the ratio of fluorinated monomers to non-fluorinated polymerizable adhesive monomer be less than 1:1, preferably less than 1:2, and more preferably less than 1:4 or less than 1:10.

Examples of suitable siloxane monomers and polymers include, but are not limited to, siloxane-containing 1,1-disubstituted ethylene monomers. Particularly preferred suitable siloxane-containing monomers and polymers include, but are not limited to, siloxane-containing α-cyanoacrylates such as alkyl α-cyanoacrylates having an alkyl chain length of from about 1 to about 20 carbon atoms, preferably from about 2 to about 12 carbon atoms. Examples of such siloxane-containing alkyl α-cyanoacrylates include, for example, siloxane-containing ethyl, butyl, and octyl α-cyanoacrylates. Other particularly preferred suitable siloxane-containing monomers and polymers include, for example, siloxane-containing cyanopentadienoates.

Preferably, where siloxane-containing cyanopentadienoates are used, it is preferred, although not required, that the compound not be a di-α-cyanopentadienoate disiloxane of the formula:

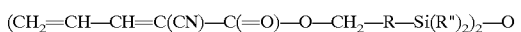

wherein R is —CH=CH— or —C(=CH$_2$)— and R" are the same or different hydrocarbon or halosubstituted hydrocarbon groups, as disclosed in U.S. Pat. No. 5,386,047 to Nakos et al., the entire disclosure of which is incorporated herein by reference. However, when such compounds are used as friction reducing agents, they are preferably used in the composition in combination with non-siloxane containing polymerizable adhesive monomers.

Suitable siloxane groups incorporated into the monomer or polymer include, but are not limited to, disiloxane having the formula —SiH$_2$—O—SiH$_3$, trisiloxane such as linear trisiloxane having the formula —(SiH$_2$—O)$_2$—SiH$_3$ or branched trisiloxane having the formula —SiH(—O—SiH$_3$)$_2$, or linear or branched longer siloxane units such as those having the formulas —(SiH$_2$—O)$_n$—SiH$_3$, —(Si(CH$_3$)$_2$—O)$_n$—SiH$_3$, —(Si(CH$_3$)$_2$—O)$_n$—Si(CH$_3$)$_3$, or —SiH(—O—SiH$_3$)$_n$(—O—SiH$_3$)$_m$, where n and m are integers of any suitable number to provide a desired molecular weight of the monomer. For example, n and m can independently be an integer of from about 1 to about 100, preferably from about 1 to about 50.

Thus, for example, examples of suitable siloxane-containing α-cyanoacrylates include, but are not limited to, monomers of the formula:

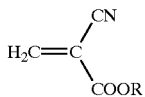

wherein R is a siloxane-containing group of the formula —(O—Si(CH$_3$)$_2$)$_n$—O—Si(CH$_3$)$_3$, where n is from about 1 to about 100, preferably from about 1 to about 50.

Polymers of the above monomeric units may also be included in the adhesive composition, in embodiments. Thus, for example, poly(siloxane-containing cyanoacrylate) can be used as a slip additive or friction reducing agent. Thus, for example, a poly(siloxane-cyanoacrylate of the following formula can be used:

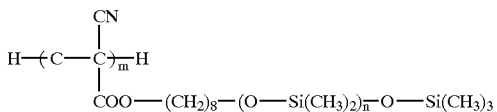

where m represents the number of repeating units in the polymer and n is from about 1 to about 100, preferably from about 1 to about 50. Where the siloxane-containing polymer is added to the adhesive composition as a separate component, the polymer is preferably a low molecular weight polymer in which m ranges, for example, from about 2 to about 2000 or more, preferably from about 2 to about 1000 or more from about 500 to about 1800, more preferably from about 100 to about 500 or from about 1000 to about 1700.

Other examples of suitable siloxane containing polymers include, but are not limited to, siloxane-containing copolyols, such as copolymers of siloxane and polyethylene glycol. Particularly suitable copolyols include dimethicone copolyol, also referred to as polydimethylsiloxane polyethylene glycol.

The dimethicone copolyol suitable for use in the present invention can include a polydimethylsiloxane (PDMS) segment that can be alkyl- or phenyl-terminated linear or cyclic or a mixture thereof. Although not limited thereto, the PDMS segment of the dimethicone copolyol used in the present invention is preferably a relatively short or small compound, as opposed to a long chain polymer. Thus, for example, the PDMS segment preferably has a low molecular weight, e.g., has a small number of monomer units, and also a low viscosity. Preferably, in embodiments, the PDMS segment is a linear compound, rather than a cyclic compound.

Still other examples of suitable siloxane containing polymers include, but are not limited to, the MASIL® series of products available from BASF Corporation and the SILWET® series of products available from Union Carbide.

When the friction reducing agent is a fluorinated monomer or a siloxane-containing monomer, it is preferred that the monomer be polymerizable with the polymerizable adhesive monomer contained in the adhesive composition. In this embodiment, the friction reducing agent will thus become an integral part of the polymer film during polymerization. However, in other embodiments, the fluorinated monomer or siloxane-containing monomer need not be polymerizable with the polymerizable adhesive monomer, and can thus exist as a separate species in the resultant polymer film.

When the friction reducing agent is a fluorinated monomer or polymer or a siloxane-containing monomer or polymer, or even any of the other friction reducing agents described herein, it is preferred that the friction reducing agent be soluble both in the polymerizable monomer of the adhesive composition, as well as in the polymer formed therefrom. However, in embodiments, it may be acceptable for the friction reducing agent to be insoluble in one or both of the polymerizable monomer of the adhesive composition, and the polymer formed therefrom.

Furthermore, in the case of the siloxane-containing monomer or polymer, it is preferred, although not required, that the compound not be a siloxane compound having a 2-cyanoacryloyl group at each end. Instead, in such cases, the compound preferable does not include any 2-cyanoacryloyl groups, although the compound may have a 2-cyanoacryloyl group at one end, but other end of the compound is preferably terminated by a different group. However, where such siloxane compounds having a 2-cyanoacryloyl group at each end are used as friction reducing agents in embodiments of the present invention, it is preferred that the compounds be used in amounts of less than 1 weight percent, or more than 50 weight percent, based on the total composition.

Suitable slip additives or friction reducing agents also include long chain fatty acid esters. By "long chain fatty acid ester" is meant a fatty acid ester having a total carbon number (i.e., total number of carbon atoms) of about thirteen or more. In embodiments of the present invention, it is believed that the long chain fatty acid esters may not necessarily reduce the coefficient of friction of the polymer film per se. However, even where the coefficient of friction of the polymer film is not directly reduced, the long chain fatty acid esters generally have the effect of forming a second phase in the polymer film. This second phase provides a more click or more slippery character to the polymer film.

Examples of suitable long chain fatty acid esters include, but are not limited to, such fatty acid esters as are commonly used in the cosmetic and pharmaceutical arts as emollients, plasticizers, lubricants, and the like. Particularly preferred suitable fatty acid esters include, but are not limited to, fatty acid esters formed from fatty acids and alcohols, where the fatty acid ester has a combined carbon number of from about 13 to about 60, preferably from about 13 to about 40 and more preferably from about 15 to about 30. Thus, for example, suitable fatty acid esters include those formed from fatty acids having a carbon chain length of from about 2 to about 30, preferably from about 4 to about 22, including but not limited to butyric acid, lauric acid, palmitic acid, stearic acid, and the like. Suitable alcohols useful in forming the fatty acid esters include, but are not limited to, alcohols having a carbon chain length of from about 2 to about 30, preferably from about 4 to about 22, including but not limited to butanol, lauryl alcohol (dodecanol or dodecyl alcohol), cetyl alcohol, stearyl alcohol (octadecyl alcohol), and the like. Accordingly, suitable fatty acid esters include, but are not limited to, compounds represented by the following general formula (III):

 (III)

where p and q independently represent integers from about 2 to about 30, preferably from about 4 to about 22, and p+q represents an integer from about 12 to about 60, preferably from about 13 to about 40, more preferably from about 15 to about 30. A particularly preferred fatty acid ester is cetyl palmitate (cetin), such as the KESSCO® 653 product, available from Stepan Company, Northfield, Ill.). Other suitable compounds include, for example octyl isononanoate, such as the KESSCO® octyl isononanoate products available from Stepan Company, and isopropyl myristate, such as the KESSCO® IPM NF products available from Stepan Company.

Various other compounds and additives can provide effects in the adhesive composition and the resultant polymer film similar to the effects provided by the long chain fatty acid esters. For example, such compounds as mineral oil, vegetable oil, and various waxes can provide the similar effect of apparent reduction of the coefficient of friction, or increase in slip properties. Such compounds are also within the scope of the slip additive or friction reducing agent of the present invention.

Various additives can also be used as slip agents or friction reducing agents according to the present invention. Thus, for example, any of the various known fluorine- and/or siloxane-containing additives including, but not limited to, antistatic agents, antitack agents, antiblocking agents, lubricants, gloss agents and release agents can be incorporated into the adhesive composition. These various additives can be either fluorine- and/or siloxane-containing, or non-fluorine- and/or siloxane-containing.

For example, a suitable fluorine-containing (fluorinated) compound of the following general formula (IV) can be used:

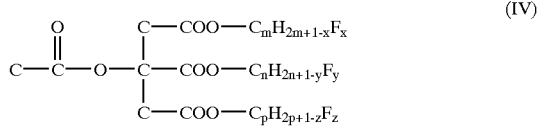

(IV)

where m, n and p are independently integers from about 1 to about 20 and x, y and z are independently integers from 1 to m, n and p, respectively. Preferably, m, n and p are independently integers from about 1 to about 15, more preferably from about 2 to about 10, and even more preferably from about 3 to about 5. Preferably, x, y and z are independently integers equal to m, n and/or p, respectively. Even more preferably, m, n, p, x, y and z are all equal. A particularly suitable compound is the compound of formula (IV) where $m=n=p=x=y=z=3$.

Various fluorinated and silyl ester compounds are known for use in adhesive compositions, particularly as anionic polymerization inhibitors. See, for example, U.S. Pat. Nos. 4,393,183 to Kimura and 5,034,456 to Katsumura et al., the entire disclosures of which are incorporated herein by reference. Such compounds can likewise be used as friction reducing agents in embodiments of the present invention. However, when so used, it is preferred, although not required, that the compound be included in an amount of greater than 1 percent by weight based on the total composition. Preferably, such compounds are included in the adhesive compositions of the present invention in amounts of at least 1.5 percent by weight, preferably at least 2 percent by weight, and more preferably at least 2.5 percent by weight or 3 percent by weight, based on the total composition.

See also, for example, U.S. Pat. No. 4,650,826 to Waniczec et al., which discloses the use of silyl esters as stabilizers or polymerization inhibitors, the entire disclosure of which is incorporated herein by reference. Such compounds can likewise be used as friction reducing agents in embodiments of the present invention. However, when so used, it is preferred, although not required, that the compound be included in an amount of greater than 3 percent by weight based on the total composition. Preferably, such compounds are included in the adhesive compositions of the present invention in amounts of at least 3.5 percent by weight, preferably at least 4 percent by weight, and more preferably at least 4.5 percent by weight or 5 percent by weight, based on the total composition.

Likewise, fluorine-containing carboxylic acid epoxy adducts are known for use in adhesive compositions. See, for example, U.S. Pat. No. 5,466,764 to Hiraoka, the entire disclosure of which is incorporated herein by reference. Such compounds can likewise be used as friction reducing agents in embodiments of the present invention. However, when so used, it is preferred, although not required, that the compound be included in an amount of less than 0.001 or greater than 10 parts by weight based on 100 parts by weight of the polymerizable adhesive monomer. Preferably, such compounds are included in the adhesive compositions of the present invention in amounts of at least 11 parts by weight, preferably at least 12 parts by weight, and more preferably at least 15 parts by weight or 20 parts by weight, based on 100 parts by weight of the polymerizable adhesive monomer.

Furthermore, in the case of the siloxane-containing additives, as with the siloxane-containing monomer or polymer described above, it is preferred that the compound not be a siloxane-containing compound having a 2-cyanoacryloyl group at each end. Instead, in such cases, the compound preferable does not include any 2-cyanoacryloyl groups, although the compound may have a 2-cyanoacryloyl group at one end, but other end of the compound is preferably terminated by a different group.

Various fluorinated polymers (or fluoropolymers or fluorocarbons) can also be used as additives in the compositions of the present invention. For example, suitable fluorocarbons include, but are not limited to, Halar® ethylene-chlorotrifluoroethylene copolymer (ECTFE) (available from Allied Chemical Corporation, Morristown, N.J.), Tefzel® ethylene-tetrafluoroethylene (ETFE) (available from E.I. duPont de Nemours and Co. Wilmington, Del.), tetrafluoroethylene (TFE), polytetrafluoroethylene (PTFE), polytetrafluoroethylene fluorinated ethylene propylene (PTFE-FEP), polytetrafluoroethylene perfluoroalkoxy (PTFE-PFA), and polyvinylidene fluoride (PVDF). While any of these and other materials can be used in the compositions of the present invention, it is preferred in embodiments that trichlorotrifluorethane, at least in an amount of from 5 to 300 parts, or 50 to 100 parts, per 100 parts of polymerizable adhesive monomer, not be used.

Preferably, when such fluorocarbons are used as a friction reducing agent, the fluorocarbon is used in the form of microparticles, which can be dispersed or solubilized in the adhesive composition. Preferably, the microparticles have a mean particle size or diameter of less than about 1000 microns, preferably less than about 100 microns, and even more preferably less than about 10 microns.

Furthermore, in embodiments where the friction reducing agent is polyvinylidene fluoride, the polyvinylidene fluoride is preferably, although not required to be, used in an amount of less than 35 parts by weight based on 100 parts by weight of the polymerizable adhesive monomer. Preferably, the polyvinylidene fluoride is used in an amount of less than 30 or less than 25 parts by weight, and more preferably less than 20 parts by weight, based on 100 parts by weight of the polymerizable adhesive monomer.

Preferably, although not required, the fluorinated polymer has a high degree of fluorine substitution in the polymer chain. Thus for example, polymers having only a low degree of fluorination, such as polymers having a polymer backbone and pendant or terminal betadiketone groups containing at least one trifluoromethyl group, such as disclosed in U.S. Pat. No. 5,039,753 to Woods et al, the entire disclosure of which is incorporated herein by reference, are less preferred and are preferably avoided, in embodiments.

Various fluorinated siloxanes can also be used as friction reducing agents in the compositions of the present invention. By fluorinated siloxanes is meant a compound containing silicon, oxygen and fluorine atoms, where the silicon atoms are bonded to a silicon atom in place of a fluorine or oxygen atom.

According to embodiments of the present invention, suitable fluorinated siloxanes includes those having a weight average molecular weight of from about 200 to about 20,000, and/or those having a viscosity, as measured at 25° C., of from about 100 to about 100,000 cP. However, fluorinated siloxanes having molecular weights and/or viscosities outside of these ranges can also be used.

Suitable fluorinated siloxanes include, for example, the fluoropropyl fluids FF157, 150-10M and F160 as well as similar products, available from GE (Waterford, N.Y.); the MED series of products, such as MED-400, MED-420 and MED-460 and similar products, available from NuSil (Carpinteria, Calif.); an d the PS series of products, such as PS 181, PS 182, PS 1836, PS 184.5, and PS 187 and similar products available from UCT (Bistol, Pa.). The MED-400 product is identified as a 100% fluorinated siloxane; the MED-420 product is identified as a copolymer of fluorosiloxane and polydimethylsiloxane, of which about 20 mol % is fluorosiloxane; and the MED-460 product is identified as a copolymer of fluorosiloxane and polydimethylsiloxane, of which about 60 mol % is fluorosiloxane.

Suitable fluorinated siloxanes include, but are in n o way limited to, fluroinated siloxanes such a s polymethyl-3,3,3trifluoropropyl siloxane of the formula:

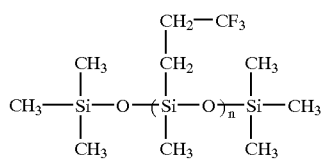

where n represents the number of repeating units and can range, for example, from about 1 to about 2000, preferably from about 2 or 10 to about 1500 or 1900, such as from about 2 to about 50 or about 100, or from about 500 or about 1000 to about 1500 or about 1800.

As for the monomers and polymers described above, although the above description has referred to the compounds as being fluorinated, the compounds are not limited thereto. Rather, any suitable halogenated compound can be used. Suitable halogens thus include fluorine, chlorine, bromine, and iodine, with fluorine being preferred, so long as they provide the desired frictional properties.

Likewise, siloxanes in and of themselves are also suitable for use as the friction reducing agent in the present invention. Thus, for example, suitable siloxanes such as octyl siloxane and octadecyl siloxane can be used. Octyl siloxane and octadecyl siloxane have the following formula:

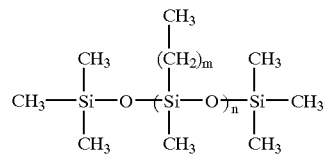

where m is 7 for octyl siloxane or 17 for octadecyl siloxane, and n represents the number of repeating units and can range, for example, from about 1 to about 2000, preferably from about 2 or 10 to about 1500 or 1900, such as from about 2 to about 50 or about 100, or from about 500 or about 1000 to about 1500 or about 1800.

In embodiments of the present invention where siloxanes are used as the friction reducing agent, it is also preferred, although not required, that the siloxane be used as a separate component in the composition, and not be added to the composition in the form of a surface treatment agent on silica or similar particles. It is also preferred, although not required, that the siloxane not have any hydrogensilyl groups. Thus, for example, it is preferred in embodiments that the siloxane be a siloxane other than acyclic hydrogenpolysiloxane compounds, such as tetramethyldisiloxane and polymethylhydrosiloxane, or a cyclic hydrogenpolysiloxane such as 1,3,5,7-tetramethylcyclotetrasiloxane. However, where such compounds are used as friction reducing agents in embodiments of the present invention, it is preferred that the compounds be used in amounts of less than 0.001 parts by weight, or more than 10 parts by weight, based on 100 parts by weight of the adhesive component, i.e., the polymerizable monomer compound.

Although the above description has referred to the monomers and polymers as being fluorinated, the monomers and polymers are not limited thereto. Rather, any suitable halogenated monomers and polymers can be used. Suitable halogens thus include fluorine, chlorine, bromine, and iodine, with fluorine being preferred, so long as they provide the desired frictional properties.

Mixtures of one or more of the above-described friction reducing agent can be used, in embodiments.

Furthermore, in the case where the friction reducing agent is a fluorinated or siloxane-containing monomer, and in particular a fluorinated or siloxane-containing 1,1-disubstituted ethylene monomer, the fluorinated or siloxane-containing monomer is preferably included in the adhesive composition in addition to a non-fluorinated or non-siloxane-containing monomer, described in greater detail below. However, acceptable results may also be achieved where the fluorinated or siloxane-containing monomer is the only polymerizable monomer species in the composition.

According to the present invention, the friction reducing agent is selected such that it is compatible with the monomer (i.e., does not adversely affect polymerization, cure properties, or shelf-life). Preferably, the friction reducing agent is soluble (i.e., dissolves) in the monomer composition at room temperature (i.e., 20–25° C.) so that it may be combined into the monomer composition without excessive heating of the monomer composition.

In embodiments of the present invention, the friction reducing agent can be soluble in the monomeric adhesive composition, but insoluble in the polymer that results from polymerization of the monomeric adhesive composition. In these embodiments, the polymer product will tend to form a two-phase system, where a first phase includes the polymer and a second phase includes the friction reducing agent. The second phase can either form immediately, or can form over time as the friction reducing agent is released or eluted from the first (polymer) phase.

Cetyl palmitate is particularly useful in forming such two-phase systems, although other of the described friction reducing agents, such as fluorinated siloxanes, can form a two-phase system as well. Producing such a two-phase system can assist in providing the reduced coefficient of friction, while at the same time permitting easier removal of the polymer film from the substrate.

Preferably, in embodiments of the present invention, the friction reducing agent has no effect, or substantially no effect, on polymerization of the polymerizable adhesive monomer. Thus, for example, when incorporated into the adhesive composition, the friction reducing agent preferably does not act, or substantially does not act, as either a polymerization inhibitor or a polymerization initiator. However, where the friction reducing agent does have such properties, the effect of the friction reducing agent can, if desired, be counterbalanced by the further addition of a compound having the opposite effect. Such suitable polymerization initiators and inhibitors are well known in the art, and can be included in known amounts for their desired effect.

Furthermore, in embodiments where desired, a friction reducing agent having polymerization inhibition effects may be desired, such that the friction reducing agent can serve the dual purpose of friction reduction in the polymer film, and polymerization inhibition in the monomer composition. However, in such embodiments, the friction reducing agent should be included in an amount such that desired polymerization is not prevented or desired cure rate and cure time are not substantially affected, and such that an effective amount of the compound remains in the resulting polymer material to provide the desired friction reduction effects.

In embodiments, the monomer composition and/or its packaging are preferably sterilized. Sterilization of the monomer composition and/or its packaging can be accomplished by techniques known to one of ordinary skill in the art, and is preferably accomplished by methods including, but not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retort canning. Examples of irradiation methods include, but are not limited to, gamma irradiation, electron beam irradiation, and microwave irradiation. A preferred method is electron beam irradiation, as described in U.S. patent application Ser. No. 09/025,472, filed on Feb. 18, 1998, the entire disclosure of which is incorporated herein by reference. The composition must show low levels of toxicity to living tissue during its useful life. In preferred embodiments of the present invention, the composition is sterilized to provide a Sterility Assurance Level (SAL) of at least $10^{-3}$. In embodiments, the Sterility Assurance Level may be at least $10^{-4}$, or may be at least $10^{-5}$, or may be at least $10^{-6}$.

The monomer (including prepolymeric) adhesive composition may include one or more polymerizable monomers. Preferred monomers that may be used in this invention are readily polymerizable, e.g. anionically polymerizable or free radical polymerizable, or polymerizable by zwitterions or ion pairs to form polymers. Such monomers include those that form polymers, that may, but do not need to, biodegrade. Such monomers are disclosed in, for example, U.S. Patents Nos. 5,328,687 and 5,928,611 to Leung et al., U.S. patent application Ser. No. 09/430,177, filed on Oct. 29, 1999, and U.S. patent application Ser. No. 09/471,392 filed Dec. 23, 1999, which are hereby incorporated in their entirety by reference herein. Preferred monomers include 1,1-disubstituted ethylene monomers, such as α-cyanoacrylates including, but not limited to, alkyl α-cyanoacrylates having an alkyl chain length of from about 1 to about 20 carbon atoms or more, preferably from about 2 to about 12 or more preferably from about 3 to about 8 carbon atoms.

The α-cyanoacrylates of the present invention can be prepared according to several methods known in the art. U.S. Patents Nos. 2,721,858, 3,254,111, 3,995,641, and 4,364,876, each of which is hereby incorporated in its entirety by reference herein, disclose methods for preparing α-cyanoacrylates.

The composition may optionally also include at least one other plasticizing agent that assists in imparting flexibility to the polymer formed from the monomer. The plasticizing agent preferably contains little or no moisture and should not significantly affect the stability or polymerization of the monomer. Examples of suitable plasticizers include but are not limited to tributyl citrate, acetyl tri-n-butyl citrate (ATBC), polymethylmethacrylate, polydimethylsiloxane, hexadimethylsilazane, isopropyl myristate, isopropyl palmitate, and others as listed in U.S. patent application Ser. No. 09/471,392 filed Dec. 23, 1999, the disclosure of which is incorporated in its entirety by reference herein.

The composition may also optionally include at least one thixotropic agent. Suitable thixotropic agents are known to the skilled artisan and include, but are not limited to, silica gels such as those treated with a silyl isocyanate, and optionally surface treated titanium dioxide. Examples of suitable thixotropic agents and thickeners are disclosed in, for example, U.S. Pat. No. 4,720,513, and U.S. patent application Ser. No. 09/374,207 filed Aug. 12, 1999, the disclosures of which are hereby incorporated in their entireties by reference herein.

The composition may optionally also include thickeners. Suitable thickeners may include poly (2-ethylhexy methacrylate), poly(2-ethylhexyl acrylate) and others as listed in U.S. patent application Ser. Nos. 09/471,392 filed Dec. 23, 1999, and 09/374,207, filed Aug. 12, 1999, the disclosures of which are incorporated by reference herein in their entirety.

The composition may also optionally include at least one natural or synthetic rubber to impart impact resistance. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties by reference herein.

The composition may optionally also include one or more stabilizers, preferably both at least one anionic vapor phase stabilizer and at least one anionic liquid phase stabilizer. The composition may optionally also include, in addition to or in place of the anionic stabilizers, at least one free radical stabilizer. These stabilizing agents may inhibit premature polymerization. Suitable anionic and free radical stabilizers may include those listed in U.S. patent application Ser. Nos. 09/471,392 filed on Dec. 23, 1999, and 09/099,457, filed Jun. 18, 1998, the disclosures of which are incorporated by reference herein in their entirety.

The stability, and thus the shelf-life, of some monomeric adhesive compositions can be further enhanced and extended through careful regulation of the packaging. Treated (e.g., fluorinated or functionalized polymer) packaging such as that disclosed in copending U.S. patent application Ser. No. 09/430,289, filed Oct. 29, 1999, which is hereby incorporated by reference herein in its entirety, is preferred and may reduce the amount of stabilizer that is combined into the composition.

The compositions may also include pH modifiers to control the rate of degradation of the resulting polymer, as disclosed in U.S. patent application Ser. No. 08/14,288, filed Sep. 18, 1996, the entire disclosure of which is hereby incorporated by reference herein in its entirety.

Compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites, etc. Additional examples of formaldehyde scavenger compounds useful in this invention and methods for their implementation can be found in U.S. Pat. Nos. 5,328,687, 5,514,371, 5,514,372, 5,575,997, 5,582,834 and 5,624,669, all to Leung et al., which are hereby incorporated herein by reference in their entireties.

To improve the cohesive strength of adhesives formed from the compositions of this invention, difunctional monomeric cross-linking agents may be added to the monomer compositions of this invention. Such crosslinking agents are known. U.S. Pat. No. 3,940,362 to Overhults, which is hereby incorporated herein in its entirety by reference, discloses exemplary cross-linking agents.

The compositions of this invention may further contain fibrous reinforcement and colorants such as dyes, pigments, and pigment dyes. Examples of suitable fibrous reinforcement include PGA microfibrils, collagen microfibrils, and others as described in U.S. patent application Ser. No. 09/471,392 filed on Dec. 23, 1999, the disclosure of which is incorporated by reference herein in its entirety.

The polymerizable compositions useful in the present invention may also further contain one or more preservatives, for prolonging the storage life of the composition. Suitable preservatives, and methods for selecting them and incorporating them into adhesive compositions, are disclosed in U.S. patent application Ser. No. 09/430,180, the entire disclosure of which is incorporated herein by reference.

In embodiments of the present invention, the composition and/or its applicator may contain additional materials such as a polymerization initiator, accelerator, rate-modifier, and/or cross-linking agent for initiating polymerization and/or cross-linking of the polymerizable monomer material. Such initiators, accelerators, rate-modifiers, and/or cross-linking agents can be included in the applicator tip, in the polymerizable composition, and/or elsewhere, as appropriate.

Suitable materials and applicators and packaging systems are disclosed in U.S. Pat. No. 5,928,611 and U.S. patent application Ser. Nos. 09/430,177, 09/430,176, 09/430,289, 09/430,290, and 09/430,180 filed Oct. 29, 1999; 09/343,914 filed Jun. 30, 1999; 09/385,030 filed Aug. 30, 1999; and 09/176,889 filed Oct. 22, 1998; the entire disclosures of which are incorporated herein by reference.

An advantage of the compositions of the present invention is that they can be better used for wound dressings and treatments. For example, the compositions of the present invention can be used as wound dressings such as for decubitus ulcers, lacerations, abrasions, burns, stomatitis, sores, large cuts, minor cuts and scrapes, and other wounds. The compositions of the present invention thus find uses in, for example, apposing surgically incised or traumatically lacerated tissues; retarding blood flow from wounds; dressing burns; dressing skin or other superficial or surface wounds such as compromised skin or other tissue (such as abrasions, chaffed or raw skin, minor cuts and scrapes, irritation, sores and/or stomatitis); protecting intact skin; and aiding repair and regrowth of living tissue. In embodiments, the compositions of the present invention can be applied to intact skin or tissue, such as to areas of skin or tissue that are prone or predisposed to irritation, injury, breakdown, and the like. For example, the compositions of the present invention can be applied to tissue that is subject to injury or irritation, such as knees, elbows, knuckles and the like; can be applied to tissue that is subject to irritation or inflammation, such as areas prone to occurrence of bed sores; can be applied to tissue for treatment, for example, of incontinence; and the like.

Monomer compositions of the present invention, and polymers formed therefrom, are also useful in industrial and home applications, for example in bonding rubbers, plastics, wood, composites, fabrics, and other natural and synthetic materials. When so used, the compositions of present invention provide a reduced coefficient of friction between the formed polymeric film and other articles that may come into contact, particularly sliding contact, with the polymeric film, such as clothing, bed sheets, casts, prostheses, bandages, and the like. The compositions of the present invention also provide the benefit that they may be more easily removed from the substrate, permitting easier and less painful removal such as for inspection, cleansing, and the like.

The following examples illustrate specific embodiments of the present invention. One skilled in the art will recognize that the appropriate reagents, and component ratios/concentrations may be adjusted as necessary to achieve specific product characteristics. All parts and percentages are by weight unless otherwise indicated.

EXAMPLES

Examples 1–3

Adhesive compositions are prepared including 2-octyl cyanoacrylate and varying percents by weight of a fluorinates siloxane (50:50 mol copolymer polydimethylsiloxane-trifluoropropylsiloxane). The compositions are formulated as shown in Table 1 below.

A film of each adhesive composition is formed and tested for its coefficient of friction, according to ASTM D-1894. The test results are shown in Table 1 below.

Comparative Example 1

An adhesive composition including only 100% 2-octyl cyanoacrylate, i.e., without any additives, is also tested for its coefficient of friction, according to ASTM D-1894. The test results are shown in Table 1 below.

Comparative Example 2

A commercial stabilized adhesive composition, DERMA-BOND® available from Closure Medical Corporation, including 2-octyl cyanoacrylate and other additives, is also tested for its coefficient of friction, according to ASTM D-1894. The test results are shown in Table 1 below.

TABLE 1

| Example | 2-octyl cyanoacrylate (wt. %) | Slip Additive (wt. %) | Static Coefficient of Friction | Dynamic Coefficient of Friction |
|---|---|---|---|---|
| 1 | 90 | 10 | 0.48 | 0.37 |
| 2 | 97 | 3 | 0.46 | 0.33 |
| 3 | 99 | 1 | 0.54 | 0.43 |

TABLE 1-continued

| Example | 2-octyl cyanoacrylate (wt. %) | Slip Additive (wt. %) | Static Coefficient of Friction | Dynamic Coefficient of Friction |
|---|---|---|---|---|
| Comp 1 | 100 | 0 | 0.87 | 0.83 |
| Comp 2 | — | 0 | 1.01 | 0.96 |

Examples 2–6

Stabilized adhesive compositions are prepared including 2-octyl cyanoacrylate and varying amounts by weight cetyl palmitate (KESSCO® 653 available from Stepan Company). The compositions are formulated as follows:

| Example | adhesive composition (g) | cetyl palmitate (g) |
|---|---|---|
| 2 | 11.94 | 0.06 |
| 3 | 11.88 | 0.12 |
| 4 | 11.82 | 0.18 |
| 5 | 11.76 | 0.24 |
| 6 | 11.70 | 0.30 |

The cetyl palmitate is added to the adhesive composition and stirred to dissolve the cetyl palmitate. After stirring, the remaining cetyl palmitate has the appearance of waxy flakes, indicating that it has partially dissolved into the adhesive composition. The composition is allowed to sit in a cabinet for several weeks. Upon removal from the cabinet, the composition has an oily layer over the adhesive composition material. The adhesive composition is filtered using a syringe filter.

7 g of the filtered adhesive composition is initiated using 110 μL of a 1% solution of benzalkonium chloride with mixing. The initiated adhesive composition is applied to a glass slide, and flattened with another glass slide.

Following polymerization, the second glass slide is removed from the first glass slide.

While the invention has been described with reference to preferred embodiments, the invention is not limited to the specific examples given, and other embodiments and modifications can be made by those skilled in the art without departing from the spirit and scope of the invention.

What is claimed is:

1. A polymerizable monomer adhesive composition, comprising:
    a 1,1-disubstituted ethylene monomer; and
    at least one slip additive,
    wherein said slip additive causes a polymer film formed from said monomer to have a lower coefficient of friction than in an absence of said slip additive, and
    wherein the slip additive is selected from the group consisting of siloxane-containing monomers; siloxane-containing copolyols; fluorinated siloxanes; a flourinated α-cyanoacrylate monomer; a flourinated cyanopentadienoate; a fluorinated polycyanpacrylate; a fluorinated polymer selected from the group consisting of ethylene-chlorotrifluoroethylene copolymer, ethylene-tetrafluoroethylene, tetrafluoroethylene, polytetrafluoroethylene, polytetrafluoroethylene fluorinated ethylene propylene, polytetrafluoroethylene perfluoroalkoxy, and polyvinylidene fluoride; and a fluorine-containing compound of the following general formula:

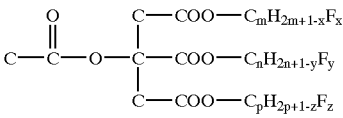

wherein m, n and p are independently intergers of from about 1 to about 20, x is independently an integer of from 1 to m, y is independently an interger of from 1 to n, and z is independently an interger of from 1 to p.

2. The composition of claim 1, wherein the coefficient of friction is a dynamic coefficient of friction.

3. The composition of claim 1, wherein the coefficient of friction is lowered by at least 30%.

4. The composition of claim 1, wherein the coefficient of friction is less than about 0.55.

5. The composition of claim 1, wherein the slip additive is soluble in the monomer.

6. The composition of claim 1, wherein the slip additive is included in an amount of from about 0.05 to about 25% by weight, based on a total weight of the composition.

7. The composition of claim 1, wherein the slip additive is a fluorinated α-cyanoacrylate monomer.

8. The composition of claim 7, wherein the fluorinated α-cyanoacrylate monomer is an alkyl α-cyanoacrylate having an alkyl chain length of from 1 to about 20 carbon atoms.

9. The composition of claim 7, wherein the fluorinated α-cyanoacrylate monomer is selected from the group consisting of fluorinated ethyl α-cyanoacrylate, fluorinated butyl α-cyanoacrylate, and fluorinated octyl α-cyanoacrylate.

10. The composition of claim 7, wherein the fluorinated α-cyanoacrylate monomer is a monomer of the formula:

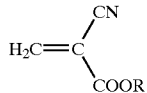

wherein R is a fluorinated alkyl group having from 1 to about 20 carbon atoms.

11. The composition of claim 10, wherein the fluorinated α-cyanoacrylate monomer is selected from the group consisting of octafluorobutyl cyanoacrylate and hexadecafluorooctyl cyanoacrylate.

12. The composition of claim 1, wherein the slip additive is a fluorinated cyanopentadienoate.

13. The composition of claim 1, wherein the slip additive is a fluorinated polycyanoacrylate.

14. The composition of claim 13, wherein the fluorinated polycyanoacrylate is represented by the formula:

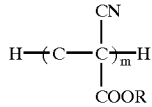

wherein R is a fluorinated alkyl group having from 1 to about 12 carbon atoms and m is an integer representing a number of repeating units in the fluorinated polycyanoacrylate.

15. The composition of claim 14, wherein R is selected from the group consisting of $C_4HF_8$ and $C_8HF_6$.

16. The composition of claim 1, wherein the slip additive is a siloxane-containing monomer.

17. The composition of claim 16, wherein the siloxane-containing monomer is polymerizable with the 1,1-disubstituted ethylene monomer.

18. The composition of claim 16, wherein the siloxane-containing monomer is not polymerizable with the 1,1-disubstituted ethylene monomer.

19. The composition of claim 1, wherein the slip additive is a siloxane-containing 1,1-disubstituted ethylene monomer.

20. The composition of claim 1, wherein the slip additive is a siloxane-containing α-cyanoacrylate monomer.

21. The composition of claim 20, wherein the siloxane-containing α-cyanoacrylate monomer is an alkyl α-cyanoacrylate having an alkyl chain length of from 1 to about 20 carbon atoms.

22. The composition of claim 20, wherein the siloxane-containing α-cyanoacrylate monomer is selected from the group consisting of siloxane-containing ethyl α-cyanoacrylate, siloxane-containing butyl α-cyanoacrylate, and siloxane-containing octyl α-cyanoacrylate.

23. The composition of claim 20, wherein the siloxane unit in the siloxane-containing α-cyanoacrylate monomer is selected from the group consisting of disiloxane, linear trisiloxane and branched trisiloxane.

24. The composition of claim 1, wherein the slip additive is a siloxane-containing cyanopentadienoate.

25. The composition of claim 1, wherein the slip additive is a siloxane-containing copolyol.

26. The composition of claim 25, wherein the siloxane-containing copolyol is dimethicone copolyol.

27. The composition of claim 25, wherein the siloxane-containing copolyol is a copolymer of polydimethylsiloxane and polyethylene glycol.

28. The composition of claim 1, wherein the slip additive is a fluorine-containing compound of the following general formula:

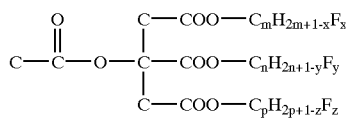

wherein m, n and p are independently integers of from about 1 to about 20, x is independently an integer of from 1 to m, y is independently an integer of from 1 to n, and z is independently an integer of from 1 to p.

29. The composition of claim 28, wherein m=n=p=x=y=z=3.

30. The composition of claim 1, wherein the slip additive is a fluorinated polymer selected from the group consisting of ethylene-chlorotrifluoroethylene copolymer, ethylene-tetrafluoroethylene, tetrafluoroethylene, polytetrafluoroethylene, polytetrafluoroethylene fluorinated ethylene propylene, polytetrafluoroethylene perfluoroalkoxy, and polyvinylidene fluoride.

31. The composition of claim 30, wherein the slip additive is in a form of microparticles.

32. The composition of claim 1, wherein the slip additive is in a form of polytetrafluorethylene microparticles.

33. The composition of claim 1, wherein the slip additive is a fluorinated siloxane.

34. The composition of claim 1, wherein the slip additive is a siloxane selected from the group consisting of octyl siloxane and octadecyl siloxane.

35. The composition of claim 1, wherein the slip additive is compatible with the monomer and is soluble in the monomer composition at room temperature.

36. The composition of claim 35, in the slip additive is insoluble in a polymer formed from said 1,1-disubstituted ethylene monomer.

37. The composition of claim 1, wherein the 1,1-disubstituted monomer is an α-cyanoacrylate monomer.

38. The composition of claim 1, wherein the 1,1-disubstituted monomer is an ethyl α-cyanoacrylate, butyl α-cyanoacrylate, or octyl α-cyanoacrylate monomer.

39. A polymer film formed from the composition of claim 1.

40. A method of producing a polymer film, comprising:
applying the composition of claim 1 to a substrate, and allowing the composition to polymerize.

41. The method of claim 40, wherein said substrate is tissue having one or more of a decubitus ulcer, a laceration, an abrasion, a burn, a stomatitis, a sore, a large cut, a minor cut, and a scrape, or to tissue that is predisposed to skin breakdown.

42. A two-phase polymerizable monomeric adhesive composition, comprising:
a first phase comprising a 1,1-disubstituted ethylene monomer; and
a second phase comprising a slip additive,
wherein said second phase is soluble in said first phase but said second phase is insoluble or substantially insoluble in a polymer formed from said monomer, and
wherein the slip additive is selected from the group consisting of siloxane-containing monomers; siloxane-containing copolyols; fluorinated siloxanes; a fluorinated α-cyanoacrylate monomers; siloxane-containing copolyols; fluorinated siloxanes; a fluorinated α-cyanoacrylate monomer; a fluorinated cyanopentadienoate; a fluorinated polycyanpacrylate; a fluorinated polymer selected from the group consisting of ethylene-chlorotrifluoroethylene coplymer, ethylene-tetrafluoroethylene, tetrafluoroethylene, polytetrafluoroethylene, polytetrafluoroethylene fluorinated ethylene propylene, polytetrafluoroethylene perfluoroalkoxy, and polyvinylidene fluoride; and a fluorine-containing compound of the following general formula:

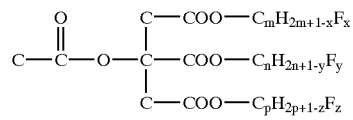

wherein m, n and p are independently intergers of from about 1 to about 20, x is independently an integer of from 1 to m, y is independently an interger of from 1 to n, and z is independently an interger of from 1 to p.

43. The composition of claim 42, wherein said second phase causes said polymer to have a lower coefficient of friction than in an absence of said second phase.

44. The composition of claim 43, wherein the coefficient of friction is lowered by at least 30%.

45. The composition of claim 43, wherein the coefficient of friction is less than about 0.55.

46. The composition of claim 43, wherein the slip additive is a fluorinated polycyanoacrylate.

47. The composition of claim 46, wherein the fluorinated polycyanoacrylate is represented by the formula:

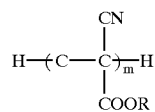

wherein R is a fluorinated alkyl group having from 1 to about 20 carbon atoms and m is an integer representing a number of repeating units in the fluorinated polycyanoacrylate.

48. The composition of claim 47, wherein R is selected from the group consisting of $C_4HF_8$ and $C_8HF_{16}$.

49. The composition of claim 42, wherein the slip additive is a siloxane-containing copolyol.

50. The composition of claim 49, wherein the siloxane-containing copolyol is dimethicone copolyol.

51. The composition of claim 49, wherein the siloxane-containing copolyol is a copolymer of polydimethylsiloxane and polyethylene glycol.

52. The composition of claim 42, wherein the slip additive is a fluorine-containing compound of the following general formula:

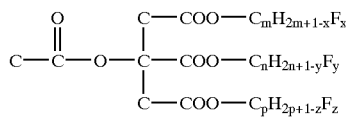

wherein m, n and p are independently integers of from about 1 to about 20, x is independently an integer of from 1 to m, y is independently an integer of from 1 to n, and z is independently an integer of from 1 to p.

53. The composition of claim 52, wherein m=n=p=x=y=z=3.

54. The composition of claim 42, wherein the slip additive is a fluorinated polymer selected from the group consisting of ethylene-chlorotrifluoroethylene copolymer, ethylene-tetrafluoroethylene, tetrafluoroethylene, polytetrafluoroethylene, polytetrafluoroethylene fluorinated ethylene propylene, polytetrafluoroethylene perfluoroalkoxy, and polyvinylidene fluoride.

55. The composition of claim 54, wherein the slip additive is in a form of microparticles.

56. The composition of claim 42, wherein the slip additive is in a form of polytetrafluoroethylene microparticles.

57. The composition of claim 42, wherein the slip additive is a fluorinated siloxane.

58. The composition of claim 42, wherein the slip additive is a siloxane selected from the group consisting of octyl siloxane and octadecyl siloxane.

59. A polymer film formed from the composition of claim 42.

60. A method of producing a polymer film, comprising:
applying the composition of claim 42 to a substrate, and allowing the composition to polymerize.

61. the method of claim 60, wherein said substrate is tissue having one or more of a decubitus ulcer, a laceration, an abrasion, a burn, a stomatitis, a sore, a large cut, a minor cut, and a scrape, or to tissue that is predisposed to skin breakdown.

62. A two-phase polymerizable monomeric adhesive composition, comprising:
a first phase comprising a 1,1-disubstituted ethylene monomer; and
a second phase comprising a slip additive,
wherein said second phase is soluble in said 1,1-disubstituted ethylene monomer but is insoluble or substantially insoluble in said polymer, and
wherein the slip additive is selected from the group consisting of siloxane-containing monomers; siloxane-containing copolyols; fluorinated siloxanes; a fluorinated α-cyanoacrylate monomer; a flourinated cyanopentadienoate; a fluorinated polycyanpacrylate; a fluorinated polymer selected from the group consisting of ethylene-chlorotrifluoroethylene copolymer, ethylene-tetrafluoroethylene, tetrafluoroethylene, polytetrafluoroethylene, polytetrafluoroethylene fluorinated ethylene propylene, polytetrafluoroethylene perfluoroalkoxy, and polyvinylidene fluoride; and a fluorine-containing compound of the following general formula:

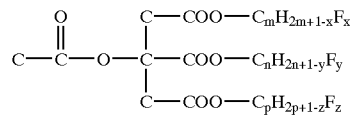

wherein m, n and p are independently intergers of from about 1 to about 20, x is independently an integer of from 1 to m, y is independently an interger of from 1 to n, and z is independently an interger of from 1 to p.

63. The composition of claim 62, wherein said second phase causes said polymeric composition to have a lower coefficient of friction than in an absence of said second phase.

64. The composition of claim 63, wherein the coefficient of friction is lowered by at least 30%.

65. The composition of claim 63, wherein the coefficient of friction is less than about 0.55.

66. The composition of claim 62, wherein the slip additive is a fluorinated polycyanoacrylate.

67. The composition of claim 66, wherein the fluorinated polycyanoacrylate is represented by the formula:

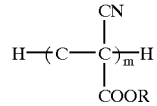

wherein R is a fluorinated alkyl group having from 1 to about 20 carbon atoms and m is an integer representing a number of repeating units in the fluorinated polycyanoacrylate.

68. The composition of claim 67, wherein R is selected from the group consisting of $C_4HF_8$ and $C_8HF_{16}$.

69. The composition of claim 62, wherein the slip additive is a siloxane-containing copolyol.

70. The composition of claim 69, wherein the siloxane-containing copolyol is dimethicone copolyol.

71. The composition of claim 69, wherein the siloxane-containing copolyol is a copolymer of polydimethylsiloxane and polyethylene glycol.

72. The composition of claim 71, wherein the polydimethylsiloxane is alkyl-terminated or phenyl-terminated.

73. The composition of claim 62, wherein the slip additive is a fluorine-containing compound of the following general formula:

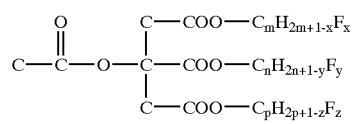

wherein m, n, and p are independently intergers of from about 1 to about 20, x is independently an integer of from 1 to m, y is independently an interger of from 1 to n, and z is independently an interger of from 1 to p.

74. The composition of claim 73, wherein m=n=p=x=y=z=3.

75. The composition of claim 62, wherein the slip additive is a fluorinated polymer selected from the group consisting of ethylene-chlorotrifluoroethylene copolymer, ethylene tetrafluoroethylene, tetrafluoroethylene, polytetrafluoroethylene, polytetrafluoroethylene fluorinated ethylene propylene, polytetrafluoroethylene perfluoroalkoxy, and polyvinylidene fluoride.

76. The composition of claim 75, wherein the slip additive is in a form of microparticles.

77. The composition of claim 62, wherein the slip additive is in a form of polytetrafluoroethylene microparticles.

78. The composition of claim 62, wherein the slip additive is a fluorinated siloxane.

79. The composition of claim 62, wherein the slip additive is a siloxane selected from the group consisting of octyl siloxane and octadecyl siloxane.

80. The composition of claim 1, wherein the polymerizable monomer adhesive composition is in a form of a two-phase composition, wherein said 1,1-disubstituted ethylene monomer is in a first phase, and said at least one slip additive is in a second phase.

81. The composition of claim 80, wherein said second phase is soluble in said first phase but said second phase is insoluble or substantially insoluble in a polymer formed from said monomer.

82. A polymerizable monomer adhesive composition, comprising:

a 1,1-disubstituted ethylene monomer; and at least one slip additive, wherein said slip additive causes a polymer film formed from said monomer to have a lower coefficient of friction than in an absence of said slip additive, and wherein the coefficient of friction is lowered by at least 30%.

83. The composition of claim 82, wherein the slip additive is selected from the group consisting of fluorinated monomers, fluorinated polymers, fluorinated additives, siloxane-containing monomers, siloxane-containing polymers, siloxane-containing additives, fluorinated siloxanes, and long chain fatty acid esters.

84. The composition of claim 82, wherein the slip additive is a fluorinated polycyanoacrylate.

85. The composition of claim 82, wherein the slip additive is a siloxane-containing copolyol.

86. The composition of claim 82, wherein the slip additive is a long chain fatty acid ester having a carbon number of at least 13.

87. The composition of claim 82, wherein the slip additive is a fluorine-containing additive or a siloxane-containing additive.

88. The composition of claim 82, wherein the slip additive is an additive selected from the group consisting of antistatic agents, antitack agents, antiblocking agents, lubricants, gloss agents, and release agents.

89. The composition of claim 82, wherein the slip additive is a fluorine-containing compound of the following general formula:

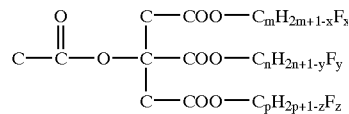

wherein m, n and p are independently integers of from about 1 to about 20, x is independently an integer of from 1 to m, y is independently an integer of from 1 to n, and z is independently an integer of from 1 to p.

90. The composition of claim 82, wherein the slip additive is a fluorinated polymer selected from the group consisting of ethylene-chlorotrifluoroethylene copolymer, ethylene-tetrafluoroethylene, tetrafluoroethylene, polytetrafluoroethylene, polytetrafluoroethylene fluorinated ethylene propylene, polytetrafluoroethylene perfluoroalkoxy, and polyvinylidene fluoride.

91. The composition of claim 82, wherein the slip additive is in a form of polytetrafluoroethylene microparticles.

92. The composition of claim 82, wherein the slip additive is a fluorinated siloxane.

93. The composition of claim 82, wherein the slip additive is a siloxane selected from the group consisting of octyl siloxane and octadecyl siloxane.

94. The composition of claim 1, wherein the slip additive is a fluorinated alkyl α-cyanoacrylate monomer.

95. The composition of claim 1, wherein the slip additive is a fluorinated alkyl α-cyanopentadienoate.

96. The composition of claim 42, wherein the slip additive is a fluorinated alkyl α-cyanoacrylate monomer.

97. The composition of claim 42, wherein the slip additive is a fluorinated alkyl α-cyanopentadienoate.

98. The composition of claim 62, wherein the slip additive is a fluorinated alkyl α-cyanoacrylate monomer.

99. The composition of claim 62, wherein the slip additive is a fluorinated alkyl α-cyanopentadienoate.

* * * * *